United States Patent
De Beenhouwer et al.

(10) Patent No.: US 11,927,586 B2
(45) Date of Patent: Mar. 12, 2024

(54) ITEM INSPECTION BY RADIATION IMAGING USING AN ITERATIVE PROJECTION-MATCHING APPROACH

(71) Applicants: UNIVERSITEIT ANTWERPEN, Antwerp (BE); IMEC VZW, Leuven (BE)

(72) Inventors: Jan De Beenhouwer, Geraardsbergen (BE); Jan Sijbers, Duffel (BE)

(73) Assignees: UNIVERSITEIT ANTWERPEN, Antwerp (BE); IMEC VZW, Leuven (BE)

(*) Notice: Subject to any disclaimer, the term of this patent is extended or adjusted under 35 U.S.C. 154(b) by 631 days.

(21) Appl. No.: 17/252,145

(22) PCT Filed: Jul. 1, 2019

(86) PCT No.: PCT/EP2019/067600
§ 371 (c)(1),
(2) Date: Dec. 14, 2020

(87) PCT Pub. No.: WO2020/002705
PCT Pub. Date: Jan. 2, 2020

(65) Prior Publication Data
US 2021/0116434 A1 Apr. 22, 2021

(30) Foreign Application Priority Data

Jun. 29, 2018 (EP) .................................... 18180893

(51) Int. Cl.
*G06K 9/00* (2022.01)
*G01N 23/046* (2018.01)
(Continued)

(52) U.S. Cl.
CPC ......... *G01N 33/367* (2013.01); *G01N 23/046* (2013.01); *G06T 7/0004* (2013.01);
(Continued)

(58) Field of Classification Search
None
See application file for complete search history.

(56) References Cited

U.S. PATENT DOCUMENTS 7,251,306 B2 7/2007 Sauer et al.
9,824,435 B2* 11/2017 Hishida ................ G01N 23/046
(Continued)

FOREIGN PATENT DOCUMENTS

WO 2016003957 A2 1/2016
WO 2016182550 A1 11/2016
(Continued)

OTHER PUBLICATIONS

Redenbach et al. "Statistical analysis and stochastic modelling of fibre composites" (Year: 2010).*
(Continued)

*Primary Examiner* — Soo Jin Park
(74) *Attorney, Agent, or Firm* — Amster, Rothstein & Ebenstein LLP

(57) ABSTRACT

A method and system for inspection of an item, and a use thereof, are presented. The method comprises acquiring a plurality of projection images of an item at a plurality of projection angles for performing a tomographic reconstruction of the item. A plurality of objects are detected in the tomographic reconstruction and each object has a generic shape described by a parametric three-dimensional numerical model. Said detection comprises determining initial estimates of position and/or orientation of each object and at least one geometrical parameter of the three-dimensional model for each object. The initial estimates are iteratively refining by using a projection-matching approach, in which forward projection images are simulated for the objects according to operating parameters of the radiation imaging device and a difference metric between acquired projection (Continued)

images and simulated forward projection images is reduced at each iteration step.

16 Claims, 9 Drawing Sheets

(51) Int. Cl.
*G01N 33/36* (2006.01)
*G06T 7/00* (2017.01)

(52) U.S. Cl.
CPC . *G01N 2223/401* (2013.01); *G01N 2223/405* (2013.01); *G01N 2223/419* (2013.01); *G06T 2207/30124* (2013.01)

(56) References Cited

U.S. PATENT DOCUMENTS

| | | | |
|---|---|---|---|
| 10,520,452 B2* | 12/2019 | Van Dael | G01N 33/025 |
| 2017/0186195 A1 | 6/2017 | Lin et al. | |
| 2018/0150929 A1 | 5/2018 | Pheiffer et al. | |
| 2019/0011254 A1 | 1/2019 | Nielsen et al. | |

FOREIGN PATENT DOCUMENTS

| | | |
|---|---|---|
| WO | 2017108689 A1 | 6/2017 |
| WO | 2020002704 A1 | 1/2020 |

OTHER PUBLICATIONS

Altendorf et al. "Stochastic modeling of a glass fiber reinforced polymer" (Year: 2011).*
Andra et al. "Geometric and mechanical modeling of fiber-reinforced composites" (Year: 2014).*
TeBmann et al. "Automatic determination of fiber-length distribution in composite material using 3D CT data" (Year: 2010).*
Brock, R.S. Reconstruction of a cone-beam CT image via forward iterative projection matching. Med. Phy. 37(12): 6212-6220, 2010.
International Search Report and Written Opinion dated Oct. 21, 2019 from PCT International Appln. PCT/EP2019/067600.
Kastner J. et al., High resolution X-ray CT of fibre and particle filled polymers. ICT Conference 2014, 16 pages, Feb. 28, 2014.
Kastner, J. et al. Pipeline zur dreidimensionalen Auswertung und Visualisierung der Faserverteilung in glasfaserverstarkten Kunststoffteilen aus u-Rontgen-Computertomografiedaten. DACH-Jahrestagung 2008 in St. Gallen—Di.3.A.1, 8 pages, Jan. 1, 2008. (A concise explanation of relevance can be found in the PCT Written Opinion submitted herewith.).
Garcea, S.C. et al. X-ray computed tomography of polymer composites. Composites Science and Technology 156: 305-319, 2018.

* cited by examiner

ITEM INSPECTION BY RADIATION IMAGING USING AN ITERATIVE PROJECTION-MATCHING APPROACH

CROSS-REFERENCE TO RELATED APPLICATIONS

This application is a U.S. national stage entry under 35 U.S.C. § 371 of PCT International Patent Application No. PCT/EP2019/067600, filed Jul. 1, 2019, which claims priority to European Patent Application No. 18180893.2, filed Jun. 29, 2018, the contents of each of which are incorporated herein by reference in their entirety.

FIELD OF THE INVENTION

The invention relates to the field of non-destructive testing of an item, such as a manufactured good, by radiation imaging. More specifically, it relates to a method and system for inspections of composite items which comprise a fibre-network structure by radiation imaging, e.g. by terahertz imaging or ionizing radiation imaging, such as X-ray imaging. The invention further relates to the use of such method or system for quality control, testing, metrology, or selection.

BACKGROUND OF THE INVENTION

In textiles comprising fibers and fiber-reinforced polymers, the orientation of the individual fibers relative to each other is greatly influencing the final product properties, in particular the strength and stiffness of the textile or a fiber-reinforced composite material. Obtaining the desired product properties is critical for safety-related aspects in automotive or aeronautics applications. Therefore, an inspection of the fibers and their orientation, as well as the detection of regions of fiber misalignment, is an important step in assessing the quality of a manufacturing process such as injection molding, in which a local fiber orientation is susceptible to be changed during a flow phase and subsequent cooling phase. Known methods for inspecting fibers and their orientation are based on optical inspection via optical microscopy. These methods have the disadvantage of being destructive and providing only two-dimensional information on the fiber orientation.

Segmentation of fiber containing materials in a 3D reconstruction from an X-ray computed tomography scan often introduces numerous artefacts during the reconstruction process, for instance artefacts that are due to many fibers are intersecting or touching each other if the fiber content is high. This tends to make the segmentation of the individual fibers a difficult problem and can lead to virtual fiber breakage, false fiber connection, multi fiber merging, etc., in the reconstructed 3D images.

SUMMARY OF THE INVENTION

It is an object of embodiments of the present invention to provide reliable non-destructive means and methods for item inspection.

The above objective is accomplished by a method and device according to the present invention.

In a first aspect, the present invention relates to a method for inspection of an item. The method comprises the following steps:

acquiring a plurality of projection images of the item at a plurality of projection angles, using a radiation imaging device;

obtaining a tomographic reconstruction based on the plurality of projection images;

detecting a plurality of objects, e.g. fibers, in the tomographic reconstruction, each object having a generic shape described by a parametric three-dimensional numerical model, wherein said detecting comprises determining initial estimates of position and/or orientation of each of said plurality of objects and at least one geometrical parameter of said three-dimensional model for each of said plurality of objects;

iteratively refining said initial estimates by using a projection-matching approach, wherein said refining comprises, at each iteration, simulating forward projection images according to operating parameters of the radiation imaging device at said plurality of projection angles for at least one of the plurality of objects, and reducing a difference metric between acquired projection images and simulated forward projection images.

The method allows, but does not require, to only partially project an object, e.g. a single fiber or a limited number of fibers, while keeping the other objects, e.g. fibers, fixed. This partial projection allows for a more efficient approach where only a single object is refined and only a small portion is forward projected In a method in accordance with embodiments of the first aspect of the present invention, said three-dimensional numerical model may be a cylinder.

In a method in accordance with embodiments of the first aspect of the invention, said determining of said initial estimates may comprise determining a center position and a direction of each of said plurality of objects and a length and/or a radius of each of said plurality of objects.

In a method in accordance with embodiments of the first aspect of the invention, said objects may be numerically modeled as fibers.

In a method in accordance with embodiments of the first aspect of the invention, said item may be a fiber-reinforced composite in which said fibers are embedded in a matrix substance, such as a polymer or resin matrix.

In a method in accordance with embodiments of the first aspect of the invention, said acquiring of the plurality of projection images may comprise performing a (micro-)computed tomography scan of the item.

It is an advantage of a method in accordance with embodiments of the present invention that it can do with fewer projection images than a conventional method. For instance, in a method in accordance with embodiments of the first aspect of the invention, the plurality of projection images may consist of a number of projection images, wherein the number lies in the range of 5 to 1000, preferably in the range of 10 to 200.

In a method in accordance with embodiments of the first aspect of the invention, said step of reconstructing may comprise performing an algebraic tomographic reconstruction technique.

In a method in accordance with embodiments of the first aspect of the invention, said algebraic tomographic reconstruction technique may comprise a Simultaneous Iterative Reconstruction Technique.

In a method in accordance with embodiments of the first aspect of the invention, said detecting may comprise segmenting said objects from an image background in said tomographic reconstruction.

In a method in accordance with embodiments of the first aspect of the invention, said segmenting may comprise a template matching of the tomographic reconstruction to a template for said numerical model to obtain a resultant image of said template matching. Alternatively, this may be obtained by a machine learning method, wherein the tomographic reconstruction is applied as input to a machine learning algorithm trained on models of object shapes.

In a method in accordance with embodiments of the first aspect of the invention, template matching may comprise calculating a normalized cross correlation of the tomographic reconstruction to said template.

In a method in accordance with embodiments of the first aspect of the invention, said template may comprise an isotropic three-dimensional Gaussian template.

In a method in accordance with embodiments of the first aspect of the invention, said detecting may further comprise thresholding said resultant image such that voxel values in the resultant image below a predetermined threshold are set to a reference background level, e.g. to zero.

In a method in accordance with embodiments of the first aspect of the invention, said predetermined threshold may be a predetermined ratio of the maximum intensity in said resultant image.

In a method in accordance with embodiments of the first aspect of the invention, said detecting may comprise determining local maxima in said resultant image.

In a method in accordance with embodiments of the first aspect of the invention, said local maxima may be detected in a neighborhood, e.g. a 26-neighbourhood, around each voxel of said resultant image.

In a method in accordance with embodiments of the first aspect of the invention, said detecting may comprise selecting the local maxima above a predetermined value indicative of an expected attenuation value of said objects as detected objects, and associating the position of said selected local maxima to said determined initial estimate of position for each of said detected objects.

In a method in accordance with embodiments of the first aspect of the invention, associating said position may comprise computing a center of mass of the resultant image in a neighbourhood, e.g. a 26-neighbourhood, around said detected local maximum.

In a method in accordance with embodiments of the first aspect of the invention, said detecting may comprise determining said initial estimate of said position of each of said objects, and subsequently detecting said orientation of each of said objects taking the determined initial estimate of said position into account.

In a method in accordance with embodiments of the first aspect of the invention, said detecting of said orientation may comprise performing a Hough transform.

In a method in accordance with embodiments of the first aspect of the invention, said Hough transform may comprise an iterative Hough Transform algorithm for three-dimensional line segments.

In a method in accordance with embodiments of the first aspect of the invention, said detecting may comprise determining an initial estimate of the length of each of said objects after determining said initial estimate of said orientation.

In a method in accordance with embodiments of the first aspect of the invention, said determining said initial estimate of said length may comprise an edge detection on a line profile in said resultant image at said initial estimate of said position in the direction corresponding to said initial estimate of said orientation.

A method in accordance with embodiments of the first aspect of the invention may comprise applying a median filter to said line profile and/or smoothing said line profile using a Gaussian filter.

A method in accordance with embodiments of the first aspect of the invention may comprise determining inflection points on either end of said line profile.

In a method in accordance with embodiments of the first aspect of the invention, said determining of said inflection points may comprise a B-spline interpolation and calculating the roots of the 2nd spatial derivative for which the highest slope in the 1st spatial derivative is found.

In a method in accordance with embodiments of the first aspect of the invention, determining said inflection points may comprise determining candidate inflection points and rejecting candidate inflection points for which the slope is below a predetermined threshold.

In a method in accordance with embodiments of the first aspect of the invention, said predetermined threshold may be a predetermined value between an expected attenuation value of a background material in said item and an expected attenuation value of said objects.

In a method in accordance with embodiments of the first aspect of the invention, said refining of said initial estimates by iteration may comprise a numerical optimization of parameters comprising said position and/or orientation of each of said plurality of objects and said least one geometrical parameter for each of said plurality of objects using said initial estimate as initialization parameters for said optimization.

In a method in accordance with embodiments of the first aspect of the invention, said numerical optimization may be a numerical minimization of a difference or discrepancy metric, such as a least squares difference, between the plurality of projection images and the corresponding simulated forward projection images of the plurality of detected objects in a three-dimensional image volume.

A method in accordance with embodiments of the first aspect of the invention may comprise outputting said simulated three-dimensional image volume used in a final iteration of said numerical optimization.

In a method in accordance with embodiments of the first aspect of the invention, the simulated three-dimensional image may be generated by sampling said three-dimensional numerical model for each of said plurality of objects using said parameters.

In a method in accordance with embodiments of the first aspect of the invention, said optimization may optimize the parameters for one of said objects in each iteration or in a block of iterations of said optimization, while keeping the parameters for the other objects of said objects fixed.

In a method in accordance with embodiments of the first aspect of the invention, said optimization may cycle multiple times over all of said objects being optimized individually.

In a method in accordance with embodiments of the first aspect of the invention, said optimization may be a least square minimization, and wherein said parameters are optimized using a gradient descent approach using finite differences.

In a method in accordance with embodiments of the first aspect of the invention, said finite differences of each of said parameters may be optimized in the current iteration of said optimization are varied by plus and minus a finite difference step length.

In a method in accordance with embodiments of the first aspect of the invention, said finite difference step length may be decreased in absolute value if the difference or discrepancy metric did not decrease in a previous iteration with respect to the iteration before said previous iteration.

A method in accordance with embodiments of the first aspect of the invention may comprise outputting a list of parameters of said plurality of objects, wherein said parameters comprise said refined estimates of position and/or orientation of each of said plurality of objects and at least one geometrical parameter of said three-dimensional model for each of said plurality of objects.

In a second aspect, the invention relates to a system comprising a radiation imaging device and a processor, wherein said radiation imaging device is adapted for acquiring said plurality of projection images of said item at a plurality of projection angles in a method in accordance with any of the previous claims, and wherein said processor is adapted for performing the remaining steps of said method in accordance with any of the previous claims taking operating parameters of the radiation imaging device into account.

In a third aspect, the invention relates to a use of a method or system in accordance with embodiments of the first or second aspect of the present invention for quality control, testing, classification, selection, metrology, and/or sorting of each item of a plurality of items in a manufacturing or handling environment for manufacturing or manipulating the plurality of items.

A use in accordance with embodiments of the third aspect of the invention may be a use in inline, at-line, online or offline inspection of the item in an industrial process. For example, inline may refer to a direct evaluation of an item in an industrial line, e.g. on a conveyor belt or similar mechanism for processing items in a flow, online may refer to the testing of, for example a sample of the items, by diverting the items of this sample group from a primary industrial line to a secondary line for testing the items, e.g. having a lower throughput suitable for the sampled subpopulation taken from the items on the primary line, at-line and offline may refer to the extraction of a sample from the primary line for testing, without requiring a processing of the extracted samples in an automated line. A distinction between at-line and offline testing may reside in whether the sample is tested in the industrial context of the line, e.g. in the same facility, or, for the latter, in a dedicated facility, e.g. a laboratory.

In a fourth aspect, the invention relates to a computer program product for implementing, when executed on a processor, a method in accordance with any of the claims 1 to 19 when provided with said plurality of acquired projection images and operating parameters of the radiation imaging device as input.

It is an advantage of embodiments of the invention that the inspection method is non-destructive.

It is an advantage of embodiments of the invention that the inspection method can be performed inline or at-line in an industrial process. Existing inspection systems for quality control, classification, selection, and/or metrology may be improved or may benefit from an upgrade to perform a method in accordance with embodiments of the invention.

It is an advantage of embodiments of the invention that X-ray imaging techniques can be used to resolve individual fibers. Embodiments of the invention have the further advantage of providing insight into a local directional and/or orientational fiber strength.

It is an advantage of embodiments of the invention that the number of projection images/views required for tomographic reconstruction is reduced by incorporating extensive prior knowledge into an iterative reconstruction approach. The extensive prior knowledge may be incorporated by providing easy-to-parametrize numerical three-dimensional models, such as spheres or cylinders, for the plurality of objects, which advantageously speeds up the inspection method.

It is an advantage of embodiments of the invention that reconstruction artefacts can be greatly reduced, resulting in more reliable inspection results.

It is an advantage of embodiments of the invention that the quality of an object can be controlled and/or selected based on a detection, quantification, and/or classification of defects or deficiencies of this object, e.g. of internal defects or internal deficiencies.

It is an advantage that a method or system in accordance with embodiments of the invention can be applied to identify a wide variety of objects, by providing a 3D model of the object of interest as prior knowledge.

It is a further advantage of embodiments of the present invention that a high throughput speed can be achieved, e.g. due to the relatively few projection views necessary for performing a tomographic reconstruction in inspection methods according to embodiment of the invention. It is a yet further advantage that inline applications, such as automated quality control and/or selection of objects which are inline transported in a conveying system, are feasible due to the high throughput speeds achievable.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
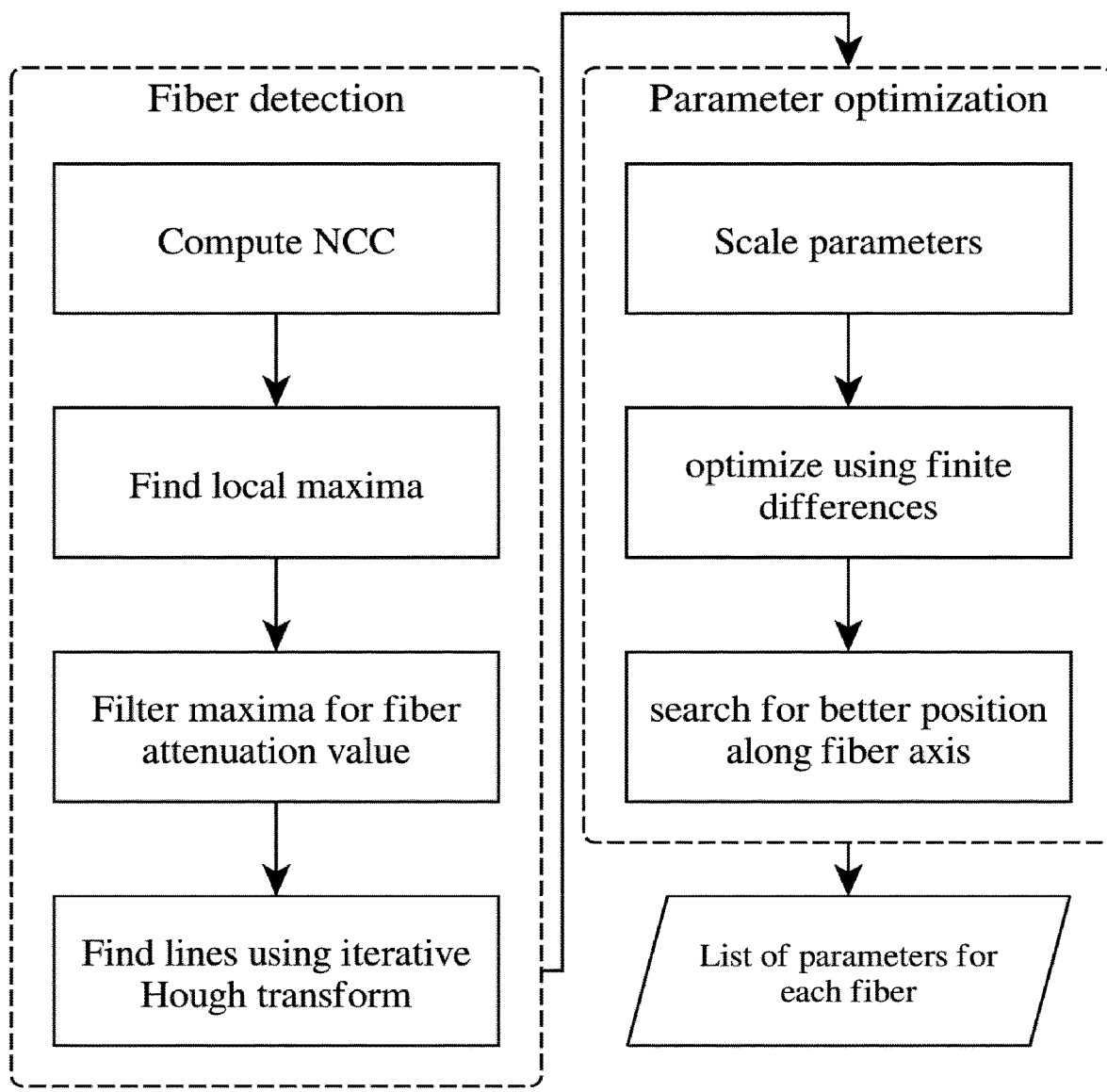
FIG. 1 shows a flowchart of a fiber detection and parameter optimization, in an example illustrating embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to a method, e.g. a computer-implemented method, for inspection of an item. The method comprises acquiring a plurality of projection images of the item at a plurality of projection angles using radiation imaging, e.g. terahertz radiation imaging and/or ionizing radiation imaging, e.g. X-ray imaging, reconstructing the acquired projection images to obtain a tomographic reconstruction, and detecting a plurality of objects in the tomographic reconstruction, in which each of the plurality of objects has a generic shape described by a parametric three-dimensional numerical model. For example, the plurality of objects may have a same generic shape defined by a parametric three-dimensional numerical model, e.g. in which at least part of the geometry defined by the model is dependent on a variable parameter(s). For example, a generic shape may relate to a spherical boundary of a solid model sphere or to a boundary of a solid model polyhedron, the radius of the sphere and the scale dimension of the polyhedron, respectively, being parameters defined by the parametric three-dimensional numerical solid model. A solid model defines an interior volume, which may be defined implicitly by its outer boundary, and material parameters can be assigned to points of the interior volume, including for example material parameters indicative of radiation-matter interaction such as linear absorption coefficient, atomic Z-number, (electron) density, etc. This detecting comprises determining initial estimates of position and/or orientation of each of the plurality of objects and at least one geometrical parameter of the three-dimensional model for each of the plurality of objects. The method also comprises refining the initial estimates by using a projection matching approach. However, as shall be obvious to the skilled person, a method in accordance with embodiments may also relate to the detecting of a plurality of objects having different generic shapes, e.g. described by a plurality of object classes, each object class being defined by a corresponding three-dimensional model, e.g. a different parametric three-dimensional model, and refining, for each detected object, the initial estimates of position and/or orientation and at least one geometrical parameter of the three-dimensional model corresponding to the class of that object. The steps of detecting and refining may be performed either consecutively or concurrently for the plurality of object classes.

The method comprises acquiring a plurality of projection images of the inspected item at a plurality of different projection angles, using radiation imaging. Acquiring the plurality of projection images may comprise using ionizing radiation imaging or terahertz imaging, e.g. X-ray imaging, such as performing a micro-computed tomography scan of the item. The plurality of projection images may consist of a number of projection images in the range of 5 to 1000, preferably in the range of 10 to 200, e.g. in the range of 10 to 100, e.g. in the range of 10 to 50, e.g. in the range of 10 to 30.

The method comprises reconstructing the acquired projection images to obtain a tomographic reconstruction volumetric image of the item. This step of reconstructing may comprise performing an algebraic tomographic reconstruction (ART) technique, such as a Simultaneous Iterative Reconstruction Technique (SIRT).

The method comprises detecting a plurality of objects in the tomographic reconstruction, in which the plurality of objects have a generic shape described by a three-dimensional numerical model. For example, the three-dimensional numerical model may be a cylinder, a sphere, a cube, a cuboid, an ovoid or a platonic solid.

In an exemplary embodiment, the objects may be fibers. For example, the item may be a fiber-reinforced composite in which the fibers are embedded in a matrix substance, such as a polymer or resin matrix. The numerical model used for such fiber may be a cylinder, e.g. having a variable length and/or radius parameter. For high aspect ratio fibers, the numerical model may take a curvature of the fiber into account, e.g. may comprise a bended cylinder. Alternatively, a plurality of abutting rigid cylinders may be used as a numerical model for the fiber. For example, segments of a single fiber may be modelled individually as rigid cylinders and the results may be combined to provide final estimates of the total length of each fiber. Furthermore, the model may be adapted to take a structured composite into account, e.g. to approximate weaving in carbon fibers.

In other embodiments, the objects may relate to struts or pores or of a porous network structure, such as trabecular metal material for orthopedic devices or porous chemical gas sensors.

The step of detecting comprises determining initial estimates of position and/or orientation of each of the plurality of objects and at least one geometrical parameter of the three-dimensional model for each of the plurality of objects.

The step of detecting may comprise segmenting the objects from an image background in the tomographic reconstruction. For example, this segmenting may comprise a template matching of the tomographic reconstruction to a template for the numerical model to obtain a resultant volumetric image of the template matching. The template matching may comprise calculating a normalized cross correlation of the tomographic reconstruction to said template. For example, the template may comprise or consist of an isotropic three-dimensional Gaussian template.

Determining the initial estimates may comprise determining a center position and a direction of each of said plurality of objects and a length and/or a radius of each of said plurality of objects.

The step of detecting may comprise thresholding the resultant image of the template matching, such that voxel values in the resultant image below a predetermined threshold are set to a reference background level, e.g. to zero. The predetermined threshold may be a predetermined ratio of the maximum intensity in the resultant image. The step of detecting may further comprise determining local maxima in the resultant image, e.g. after the thresholding operation. For example, local maxima may be detected in a neighborhood, e.g. a 26-neighbourhood, around each voxel of the resultant image. The local maxima above a predetermined value may be selected as detected objects, in which the predetermined value is indicative of an expected attenuation value of the objects. The position of the selected local maxima may be associated with the determined position for each of the detected objects. Associating the position with the detected objects may comprise computing a center of mass of the resultant image in a neighbourhood, e.g. a 26-neighbourhood, around each detected local maximum.

After determining the initial estimate of the position of each of the objects, the step of detecting may comprise subsequently detecting the orientation of each of the objects by taking the determined initial estimate of the position into account, e.g. searching for a suitable orientation of the object around the determined initial estimate of the position.

Detecting the orientation may comprise performing a Hough transform. The Hough transform may comprise an iterative Hough Transform algorithm for three-dimensional line segments.

The step of detecting may comprise determining an initial estimate of the length of each of the objects after determining the initial estimate of its orientation.

Determining the initial estimate of the length may comprise an edge detection on a line profile in the resultant image at the initial estimate of the position in the direction corresponding to the initial estimate of the orientation.

Determining the initial estimate of the length may comprise applying a median filter to the line profile and/or smoothing the line profile using a Gaussian filter.

Determining the initial estimate of the length may comprise determining inflection points on either end of the line profile.

Determining the inflection points may comprise a B-spline interpolation and calculating the roots of the 2nd spatial derivative for which the highest slope in the 1st spatial derivative is found.

Determining the inflection points may comprise determining candidate inflection points and rejecting candidate inflection points for which the slope is below a predetermined threshold.

The method also comprises refining the initial estimates by using a projection matching approach.

Refining the initial estimates may comprise a numerical optimization of parameters, in which these parameters comprise the position and/or orientation of each of the plurality of objects and the least one geometrical parameter for each of the plurality of objects, using the initial estimates as initialization parameters for this optimization.

The numerical optimization may comprise a numerical minimization of a difference or discrepancy metric, such as a least squares difference, between the plurality of projection images and the corresponding simulated forward projection images of the plurality of detected objects in a three-dimensional image volume.

The method may comprise outputting the simulated three-dimensional image volume used in a final iteration of the numerical optimization.

The simulated three-dimensional image may be generated, e.g. regenerated and/or updated in each iteration of the optimization, by sampling the three-dimensional numerical model for each of said plurality of objects using the parameters, e.g. to construct an image volume consistent with the parameters for a current iteration of the optimization.

The optimization may optimize the parameters for one of the objects in each iteration or in each block of iterations of the optimization, while keeping the parameters for the other objects of the plurality of detected objects fixed. The optimization may cycle multiple times over all of the objects being optimized individually, embodiments of the present invention not being limited thereto.

The optimization may comprise a least square minimization. The parameters may be optimized using a gradient descent approach using finite differences. The finite differences of each of the parameters being optimized in the current iteration of the optimization may, for example, be varied by plus and minus a finite difference step length. The finite difference step length may be decreased in absolute value for a current iteration if the difference or discrepancy metric, e.g. the least squares difference, did not decrease in a previous iteration with respect to the iteration before that previous iteration.

The method may also comprise outputting a list of parameters of the plurality of objects, in which the parameters comprise the refined estimates of position and/or orientation of each of the plurality of objects and at least one geometrical parameter of the three-dimensional model, e.g. a length, for each of the plurality of objects.

It is an advantage of embodiments of the present invention that the use of a parametric numerical model, e.g. a fiber model, of which the parameters are estimated directly in the projection domain may avoid or reduce reconstruction artifacts that could otherwise influence the parameter estimation, such as the estimation of fiber positions, directions and lengths. The parameter estimation thus provided may be particularly robust even for a very small number of projections. For example, a conventional algorithm known in the art may require several thousands of projection images to estimate parameters, e.g. to compute quantities on a fiber composite specimen, while this number of required projections may be strongly reduced in a method in accordance with embodiments of the present invention.

In a second aspect, the invention relates to a system comprising a radiation imaging device, e.g. an ionizing radiation imaging device or terahertz imaging device, and a processor, in which the radiation imaging device is adapted for acquiring the plurality of projection images of the item at a plurality of projection angles in a method in accordance with embodiments of the first aspect of the invention, and in which the processor is adapted for performing, e.g. programmed to perform, the other steps of that method, taking into account the operating parameters of the radiation imaging device. Such operating parameters may comprise a radiation energy spectral distribution of the source, a source-detector distance, an item-detector distance or a magnification factor, a radiation beam shape, a spectral response curve of the detector, and others.

In a third aspect, the invention relates to a use of a method in accordance with embodiments of the first aspect of the invention, and/or of a system in accordance with embodiments of the third aspect of the present invention, for quality control, testing, classification, selection, metrology, and/or sorting of each item of a plurality of items in a manufacturing or handling environment for manufacturing or manipulating the plurality of items. For example, a metrology application may relate to measuring lengths, diameters, volumes or other geometrical and/or physical properties of an item to ensure a certain measure is within tolerances.

For example, such use may be a use in inline or offline inspection of the item in an industrial process.

In a fourth aspect, the invention relates to a computer program product for implementing, when executed on a processor, a method in accordance with embodiments of the first aspect of the invention when provided with the plurality of projection images and the operating parameters of the radiation imaging device as input.

In an example demonstrating principles of the present invention, embodiments of the present invention not being limited thereby, an approach to estimate geometry parameters of glass fibers in glass fiber-reinforced polymers from simulated X-ray micro-computed tomography scans is presented, in accordance with embodiments of the present invention. Traditionally, such parameters may be estimated using a multi-step procedure including image reconstruction, pre-processing, segmentation and analysis of features of interest. Each step in this chain introduces errors that propagate through the pipeline and impair the accuracy of the estimated parameters.

In the presently disclosed approach, a volume may be reconstructed from a low number of projection angles using an iterative reconstruction technique. Then, parameters of the fibers, such as the position, direction, number and length of the in the polymer contained fibers may be determined by incorporating a priori knowledge about the fiber shape. The shape of a fiber may be modeled as a geometric representation, e.g. a numerical model. Using simulation experiments, it is shown that this method can estimate those representations even in presence of noisy data and when only very few projection angles available.

Advanced composites such as glass fiber-reinforced polymers (GFRP) integrate highly desirable features for state-of-the-art materials such as formability, low weight, high tensile and compressive strength and cost-effectiveness, thus allowing for tailored components in many different industries. Such composites may typically consist of a matrix component (e.g. a resin matrix) and a reinforcement component (e.g. glass fibers) to achieve specific mechanical properties. X-ray micro-computed tomography ($\mu$CT) is an imaging method to study the internal structure of those composites in a nondestructive way and with high spatial resolution in the micro-scale. The resulting volumetric image is then further processed to characterize features, such as the fiber direction or spatial distribution of the fibers, which have an influence on the mechanical properties of the materials. Current methods to characterize the structural properties of GFRP from high resolution $\mu$CT images rely on a sequential work flow comprised of volumetric reconstruction from a large number of projections (typically more than 1000) and subsequent fiber segmentation and image analysis.

The reconstructed image quality may depend on several parameters, such as the number of projections and the detector resolution, as well as the acquisition geometry. Since the accuracy of the identification of fibers in the volume heavily depends on the quality of the reconstruction, a long acquisition time is typically required. Additionally, parameters within the work flow from reconstruction to individual object characterization are typically determined in an empirical way, relying mainly on the experience of researchers. That is, many parameters have to be set manually or semi-automatically, in several steps of the work flow, which may introduce additional errors. Finally, because the conventional work flow is unidirectional, any error that occurs in one of the steps will propagate through the whole pipeline.

An important source of errors is that many methods require human intervention, making them non-deterministic and very reliant on researcher experience. To provide more automated solutions for single fiber extraction and measurement of fiber quantities, many approaches have been introduced lately. Many of them involve extracting the center lines of the fibers. The individual method of extracting the center lines and the use of the data differs in the approaches.

For example, an approach known in the art may use a dictionary learning approach to extract the centers of very low resolution fibers slice by slice, relying on the unidirectional fiber direction distribution of their datasets. Another approach known in the art may use the local Eigenvalues and a circular voting approach, while yet another approach may use skeletonization to extract the center lines.

In the approach presented in this example, prior knowledge that the volume to be reconstructed contains fibers of a known shape is exploited. To that end, the fibers are modeled as cylinders whose parameters are estimated by fitting a model to the measured projection data minimizing the projection distance. Initial values of the parameters are obtained from a first reconstruction of the volume using a conventional Algebraic Reconstruction Technique (ART), followed by a template matching approach similar to the one presented in Zauner et al, in Proceedings of the 14th International Congress for Stereology and Image Analysis, Acta Stereologica, 2015. A similar model-based approach was already implemented to reconstruct the crystal lattice of a gold nanoparticle at atomic resolution from electron tomography data, see e.g. Goris et al in Nano Letters 15(10), 6996 (2015).

The presented example uses X-ray projection data simulated using the ASTRA toolbox framework, see van Aarle et al, in Optics Express 24, 25129, 2016.

CT images are reconstructed from projection data, which is acquired by measuring the intensities of the X-rays after they have passed through the sample, which attenuates the radiation. The measured intensity is related to the attenuation coefficients of the different materials in the sample by the equation $$I(s) = \int_0^{E_{max}} I_0(E) \exp\left(-\int_0^L \mu(E, \eta) d\eta\right) dE, \quad (1)$$

where $I_0(E)$ is the incident beam intensity for a given energy, $\mu$ is the energy dependent attenuation coefficient of the material in function of the distance s that the X-ray travels inside the material and I(s) is the measured intensity on the detector depending on the running length through the object that is being imaged. In what follows, monochromatic X-rays are assumed to simplify the equation to the Lambert-Beer law, even though this can obviously be extended to polychromatic X-rays in an obvious manner. From a number of X-ray projections described by Eq. (1) acquired from several angles by either rotating the X-ray source and detector or the sample, a volumetric image can be reconstructed using different methods. In this example ARTs are used, more specifically the well-known Simultaneous Iterative Reconstruction Technique (SIRT) algorithm, see e.g. Gilbert, in Journal of Theoretical Biology 36(1), 105, 1972.

Using the projection images, the presented algorithm, which will be referred to hereinbelow as parametric reconstruction (PARE), starts from an initial estimate of the reconstructed volume, obtained by performing an initial, e.g. a predetermined, number of iterations of SIRT. Afterwards, the center position, direction and length of the fibers is estimated. This information is used to build a list of rigid cylinders, representing each fiber in the volume, that was detected by extracting the center line using a template matching approach. Such template matching approach, though with a different template, has been disclosed by Zauner et al, in Proceedings of the 14th International Congress for Stereology and Image Analysis, Acta Stereologica, 2015.

The cylindrical fiber model of this example has seven parameters. The first three are the x, y and z (cartesian) components of the centroid position. The subsequent two are the spherical coordinates $(\theta, \phi)$ of the direction unit vector of the fibers axis. The last two parameters are the fibers length l and radius r. Because the manufacturing process for glass fibers allows for very precisely adjustable radii, the fiber radius may be assumed to be constant. The estimation of the cylinder parameters consists of three main steps, which will be described in further detail hereinbelow. The first step is the overall detection of fibers in the current state of the reconstruction. After detection, a first estimate of the parametric representations is obtained, which may be refined by using a projection matching approach similar to the one presented by Bleichrodt et al, in Fundamenta Informaticae 135, 1 (2014).

A flowchart of the procedure, e.g. of the fiber detection and parameter optimization steps, is shown in FIG. 1.

To find voxels that are part of a fiber, the fibers are segmented from the background. As a first step of the segmentation, a template matching is computed, for example by calculating a normalized cross correlation (NCC) C_n of the reconstructed volume I with an isotropic 3D Gaussian template G:

$$C_n(u) = \frac{\sum_x [I(x) - \overline{I}_u][G(x-u) - \overline{G}]}{\sqrt{\sum_x [I(x) - \overline{I}_u]^2 \sum_x [G(x-u) - \overline{G}]^2}}, \quad (2)$$

where x and u are the image and template coordinates respectively. The quantity $\overline{I}_u$ is the local mean within the region of the image covered by the template and $\overline{G}$ is the mean intensity of G. The algorithm used to compute Eq. (2) is an efficient implementation of the NCC described by Lewis in Vision Interface 95, 120 (1995). The Gaussian template has a standard deviation dependent on the radius of the fibers using the definition of full-width at half-maximum.

$$\sigma = \frac{r_{fiber}}{2\sqrt{2\ln 2}}, \quad (3)$$

which then gives the following formula for the Gaussian template $$G(x) = \exp\left(-\frac{4\ln 2 \|x\|^2}{r_{fiber}^2}\right). \quad (4)$$

Figure 2:
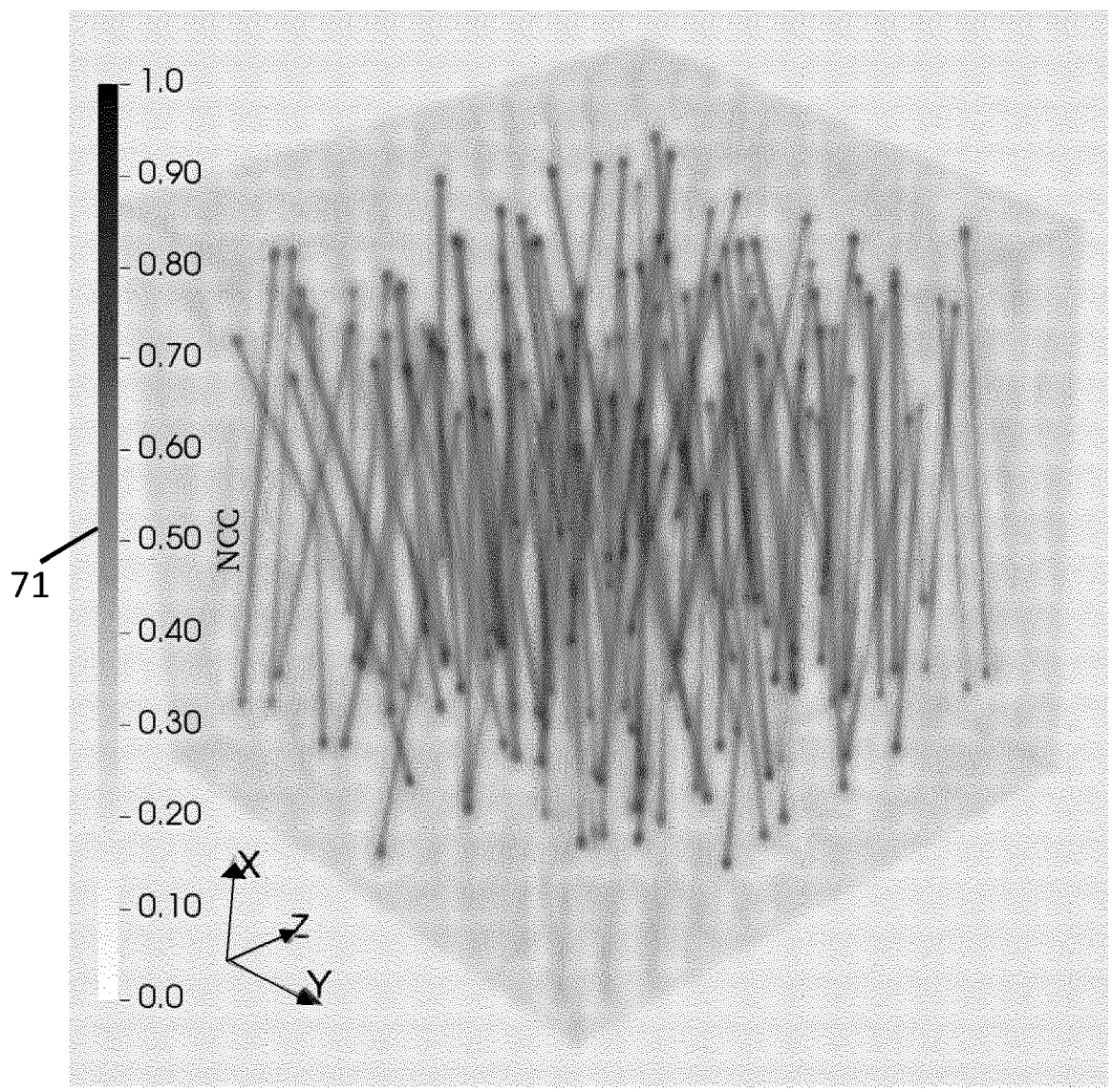
FIG. 2 shows the correlation result on the reconstructed volume of a sample phantom containing fibers with a Gaussian template in accordance with an embodiment of the present invention.

The fact that the NCC has its highest values in the location of the center line of the fiber can be exploited, which will be used to detect the direction and centroid in the step described hereinbelow. A template matching using a solid sphere has been shown to work as well by Zauner et al, in Proceedings of the 14th International Congress for Stereology and Image Analysis, Acta Stereologica (2015). With the NCC volume, the fiber center line can be detected. For that, a threshold can be applied to C_n:

$$C_{n,t}(x) = \begin{cases} C_n(x), & \text{if } C_n(x) \geq t\max_x C_n(x) \\ 0, & \text{otherwise} \end{cases} \quad (5)$$

where all voxels lower than a threshold depending on the highest peak are set to zero, but the values above or equal to the threshold are kept. The threshold value t∈[0,1] can be adjusted to the particular image, as the range of the correlation values in C_n may vary depending on the noise level in the image. The value oft gives a percentage of the maximum intensity in the NCC. For the simulations in the experiments discussed hereinbelow, a value of t=0.85 was used. In FIG. 2, the result of the NCC on the reconstructed volume of a sample phantom containing fibers (further referred to as 'phantom A') with a Gaussian template according to equation (4) is visualized. It is clear that the fibers give the highest intensity in the resulting volume and that the center line is clearly visible. It can clearly be seen that the fibers are enhanced in the resulting volume. The gradient bar 71 serves as orientation, but values below 0.55 are not rendered and values between 0.55 and 0.79 are given a transparency value for better visibility.

Then, the local maxima in C_n in the region of the 26-neighborhood around a given voxel can be obtained. The voxel values of the resulting maxima are then checked in the reconstruction, to make sure that all maxima are close to the attenuation value of the fibers. If the attenuation value is close to the expected fiber attenuation μfiber within a relative tolerance, e.g. of ±25%, the point is marked as a fiber point and refined further by computing the center of mass using the 26-neighborhood of the voxel.

From the filtered maxima of the NCC, an initial estimate of each fibers direction and centroid can be computed using the iterative Hough Transform algorithm for 3D line segments, e.g. as described by Dalitz et al in Image Processing On Line 7, 184 (2017). This algorithm differs slightly from the traditional Hough transform. The voting accumulator uses a four parameter representation of the line. The algorithm first performs the standard Hough transform algorithm on the point cloud and determines the parameters of one line using the highest peak in the accumulator. Next, it finds all points in the point cloud that lie close to the detected line and computes a least square fit of those points to get a better estimate of the line. The points close to the fitted line are removed. After this procedure, the standard Hough transform is computed on the remaining points and the above process is repeated until there are either not enough points to compute the Hough transform anymore, or the specified number of lines were detected. If this limit is not specified, the algorithm runs until the first condition is met. In this example, the Hough transform is used with a minimum of three points, but without applying a limit on the number of lines to be detected.

The angular accuracy of the iterative Hough Transform algorithm is limited by the sampling of directions and relies on the iterative subdivision of an icosahedron's faces into triangles. As a trade-off between accuracy and speed, 5 subdivisions steps can be used, which yields 5121 samples with an average spacing of 2°. As a first estimate of the direction, this may be considered as sufficiently accurate. The lines are parametrized in the form $$x = x_0 + sd \quad (6)$$

with x_0 the position vector and d the direction unit vector.

With this initial estimate, only five of the six parameters are obtained that were to be optimized, namely centroid position and direction unit vector. To also obtain an initial estimate of the length, an edge detection on a line profile through the newly estimated fiber axis can be used. This can be done using a 3-dimensional version of Bresenham's line algorithm for line voxelization on a grid, see e.g. Kaufman et al, in Proceedings of the ACM Workshop on Interactive 3D Graphics, pp. 45-75 (1986). To improve the robustness of the detection, first a median filter may be applied to remove high frequency noise while preserving the edge in the signal, and the line profile may be smoothed by a Gaussian filter with a standard deviation of r_fiber voxels. Then, the inflection points on either side of the line profile may be computed by interpolating with B-splines and, then, finding the roots of the 2nd derivative with the highest slope in the 1st derivative, see e.g. Burger et al, in Principles of Digital Image Processing: Core Algorithms (Springer, 2009) and/or Burger et al, in Principles of Digital Image Processing: Fundamental Techniques (Springer, 2009). Candidate inflection points are only considered if the slope has a higher value than a certain threshold, which can be chosen in relation to the value range between μ_fiber and μ_polymer, where μ_fiber and μ_polymer are the attenuation values for the fiber and the polymer matrix respectively. In this example, the threshold was chosen based on such intermediate intensity value of μ_polymer+0.3 (μ_fiber-μ_polymer).

Figure 3:
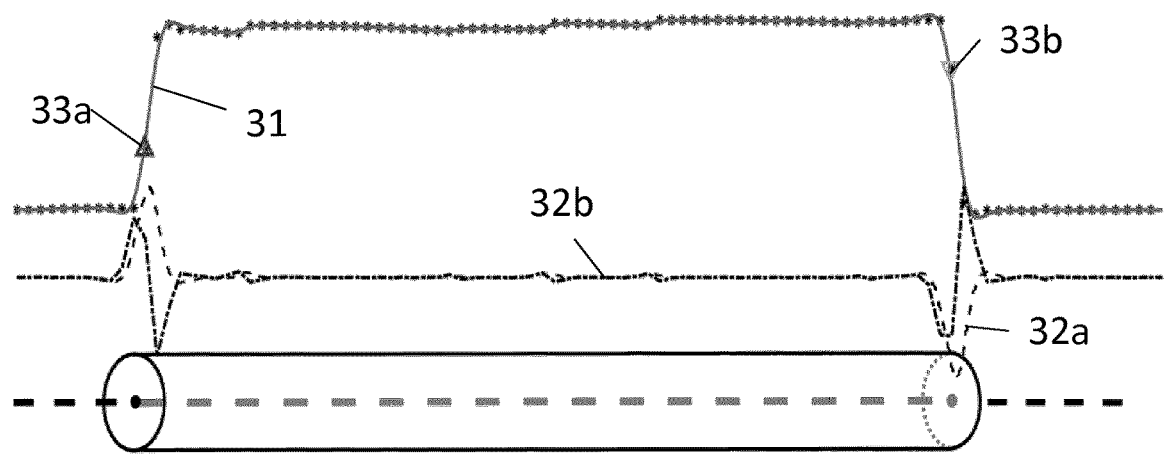
FIG. 3 shows a line profile as used in steps in an example illustrating embodiments of the present invention.

An illustration of this process with the line profile through a fiber and the interpolation with its derivatives is shown in FIG. 3. Shown is a measured line profile (marked with *), its spline interpolation 31 with 1st and 2nd derivative 32a, 32b (dashed and dash-dot lines, respectively) as well as the inflection points 33a, 33b (up-facing and down-facing triangles).

To obtain the end point positions, the two nearest whole voxel points to the detected points on the Bresenham line are linearly interpolated depending on the fraction of the inflection point's coordinate in the line profile. The initial estimate of the length is then the Euclidean distance of the two resulting end points.

With the parameter estimates from the iterative Hough transform and the length estimation as an initial starting point, a further optimization of the fiber parameters can be performed. An optimization for the components for the centroid position coordinates $$p_x = (p_{x,1}, \ldots, p_{x,N}),$$

$$p_y = (p_{y,1}, \ldots, p_{y,N}),$$

$$p_z = (p_{z,1}, \ldots, p_{z,N}),$$

for the spherical coordinates of the direction unit vector $$a_\theta = (a_{\theta,1}, \ldots, a_{\theta,N}),$$

$$a_\phi = (a_{\phi,1}, \ldots, a_{\phi,N}),$$

and for the length $$l = (l_1, \ldots, l_N),$$

for all of the N detected and estimated fibers may be performed. These may then be combined into a fiber parameter vector ξ=(p_x, p_y, p_z, a_θ, a_φ, l) and a system of linear equations may be formulated as:

$$Wx(\xi) = p, \quad (7)$$

where W is the projection matrix describing the forward projection with a fixed geometry and p is the measured projection data. The volume x, to be reconstructed, is defined as function of the fiber parameters to be estimated. Thus, the optimization of the fibers can be formulated as the minimization problem $$\arg\min_{\xi} \|Wx(\xi) - p\|^2. \quad (8)$$

which minimizes the projection distance of the forward projection of the estimated volume to the measured projection data. The minimization problem can be solved for all the acquired projection images or a subset thereof, the subset comprising at least two projection images from different projection angles.

To initialize each fiber parameter vector estimate, the data retrieved from the Hough transform in the previous step and the length computed from the detected end points is used. With this initial estimate, the parameter ranges may be scaled to the interval [0, 1] in each of the coordinates in the parameter space to make the method numerically more stable. The center of the interval, 0.5, is the initial estimate of each parameter $\xi\_i$ and the outer boundaries are given by $\xi\_i \pm \Delta\_i$.

The values for $\Delta\_i$ can be chosen empirically, e.g. to be 5 voxels (vx) for the position parameters $p\_x,i$, $p\_y,i$, $p\_z,i$. For $a\_\theta$ and $a\_$, $\Delta\_i$ can be selected as three times the spacing between two samples in the Hough accumulator and, for $l\_i$, the value can be selected as 10 vx.

The volume $x(\xi)$ to be estimated can also be pre-initialized. Given a fiber to be optimized, the N−1 remaining estimates of the fibers can be fixed and voxelized on a regular lattice grid that matches the assumed resolution of the fibers. The parameters of the fiber can then be systematically varied to optimize and voxelize the resulting fiber into the same volume. This volume is then forward projected using a forward projection method described hereinabove, e.g. using the ASTRA toolbox, and the resulting projections can be compared to the measured data.

The parameters for any given new estimate in an iteration j may be computed with an estimation of the gradient $\nabla_j$ using finite differences. To that end, $\nabla_j$ can first be initialized to zero and then each parameter can be varied $\pm\delta\_j$, e.g. where the initial value may be selected as $\delta=0.2$. If the projection error or projection distance $p\_j$ of either one of the new values for the current parameter is lower or equal to the projection error of the previous best estimate, the difference between the two values is set as the value of $\nabla_j$ for that parameter. If the projection error is not lower or equal, the gradient vector may be assumed to be zero for that particular parameter. After repeating this step for each parameter, $\nabla_j$ can be normalized to unit length and then used to compute a new estimate for the current fiber $\widetilde{\xi_i} = (\widetilde{p_{x,i}}, \widetilde{p_{y,i}}, \widetilde{p_{z,i}}, \widetilde{a_{\theta,i}}, \widetilde{a_{\varphi,i}}, \widetilde{l_i})$ as follows:

$$\xi_{i,new} = \xi_i + \nabla_j \delta. \quad (9)$$

Figure 4:
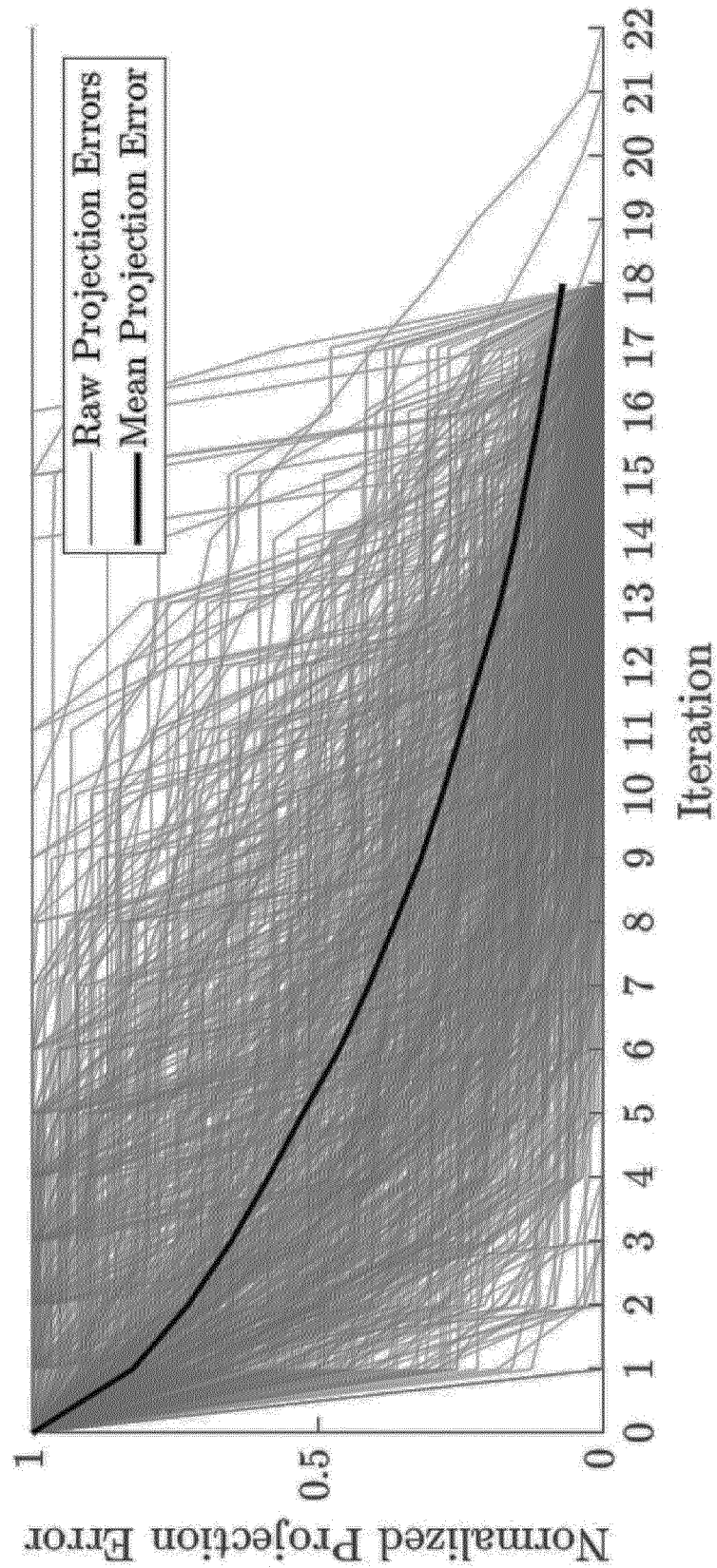
FIG. 4 shows normalized projection errors of fibers over a number of iterations, in an exemplary iterative procedure relating to embodiments of the present invention.

The projection error for the new estimate $\xi\_i,new$ is then computed. If the error is lower or equal to the error of the previous estimate, $\xi\_i,new$ is taken as the new estimate of the fiber. If the error is not lower, the delta value is decreased, e.g. to 75% of its current value. This process may be repeated for a minimum of n_min times and a maximum of n_max times. In this example, n_min=18 and n_max=35 are used, both of which were chosen empirically. The iterations stop either at the upper limit of repetitions or if the rate of change of the error, defined as $$\rho_j = 1 - \frac{p_j}{p_{j+1}}. \quad (10)$$

is lower than a threshold, e.g. a threshold of 0.001. FIG. 4 shows the normalized projection errors of 907 fibers over the number of iterations. Each thin line corresponds to a single fiber. Since the projection errors may vary drastically over the fibers, the errors were normalized, such that the convergence can be compared.

The maximum number of iterations was not reached in this example, and the error either stagnates or goes down, which shows that the fiber estimates either converge to a better solution or do not improve, if the initial estimate happens to be already sufficiently accurate, iteration 0 provides the error for the initial estimate.

To estimate the volume $x(\xi)$, the current fiber estimates are voxelized into a volume of the same size as the reconstruction. To that end, the equation of the numerical cylinder model aligned with the x axis, with the parameter radius r_fiber and the estimated length l_fiber is sampled:

$$c(x, y, z) = \begin{cases} \mu_{fiber}, & \text{if } y^2 + z^2 \leq r_{fiber}^2 \text{ and } |x| < \frac{l_{fiber}}{2} \\ \mu_{polymer}, & \text{otherwise} \end{cases} \quad (11)$$

To place the fiber in the estimated position along the estimated direction, $c(x, y, z)$ is voxelized on a regular grid which is then transformed such that the x-axis is directed along the fiber direction vector and the fiber centroid is located in the origin. Voxels that would otherwise be entirely set to μfiber may be local-adaptively subsampled, such that the voxel is subdivided n times in each coordinate direction, resulting in n3 sample points per voxel. The values of each of those sub-voxels are then computed using Eq. (11). The values obtained that way are averaged and assigned to the voxel corresponding to its set of sub-voxels, thus aliasing the fiber borders.

The voxelization can be designed in such way that it will only replace the values that are in close proximity to the fiber, so that when placing the fibers in the volume, the other fibers are not affected. This ensures that voxels are only replaced if, according to the current estimate, the voxel belongs to a fiber.

To demonstrate the PARE algorithm, two simulation experiments were set up. The numerical phantoms for those experiments were generated from a set of randomly directed fibers and with uniformly distributed centers and lengths. The fiber directions were generated as independent samples drawn from a von Mises-Fisher (vMF) distribution. Its probability density function on the sphere for a given direction $u=(\theta,\phi)$ is $$f(u;\mu_{vMF},\kappa) = C_F \exp(\kappa\mu_{vMF}^T u), \quad (12)$$

where $$C_F = \kappa/(4\pi \sin h\kappa), \quad (13)$$

and where the vector $\mu\_vMF = (\alpha,\beta)$ denotes the mean direction of the distribution and K denotes the concentration parameter, in which a large value of K corresponds to a lower variance (i.e. a higher concentration around the mean direction). The positions of the fibers are drawn from a uniform distribution, with the restriction that each fiber is fully positioned within the volume (i.e. no truncation). The fiber length was 70±10 vx, also drawn from a uniform distribution. The number of SIRT iterations was set to 100 for these experiments.

Two phantoms were generated with 100³ voxels, in which the phantoms only differ in the parameters of the direction distribution. For the first phantom, 'phantom A', the directions were drawn from $f(u,\mu=(\pi/2, 0), \kappa=40)$. The second phantom, 'phantom B', was generated from $f(u,\mu=(0,0), \kappa=7)$.

With the fibers drawn at random, a version of the Random Sequential Adsorption (RSA) algorithm was performed to generate non-overlapping fibers. To simplify the collision detection in the RSA algorithm, the fibers were treated as sphero-cylinders, reducing the collision problem to finding the closest points of two line segments and a simple distance calculation. To make the fibers behave realistically, the placement of a fiber is also kept if the fibers touch exactly, so if the distance of two fibers is exactly $d\_1,2=r\_1+r\_2$. As the aspect ratios of the fibers are high, the error introduced by this approach is negligible. Due to the higher variance around the mean direction for 'phantom B', the RSA only placed 72 fibers, while 'phantom A' contains 109 fibers. In both cases the algorithm was initialized to place 150 fibers. The expected values for both matrix and fiber attenuation were estimated from scans of a real dataset. The background had an intensity of $\mu\_polymer=[0.23\pm0.07]$ and the fibers had a normalized intensity of $\mu\_fiber=[0.76\pm0.05]$. Both intensity values are given as percentages of the maximum possible value of the used integer data type. Therefore, to generate the phantoms, the value 0.23 was used for the background and 0.76 for the fibers.

Figure 5:
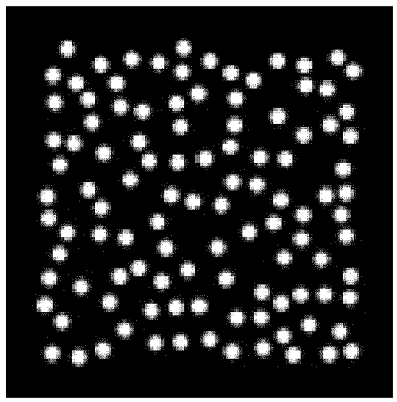
FIG. 5 and FIG. 6 show a central slice of two randomly generated phantoms and the same slice of a reconstruction of that phantom from simulated projections, in an example illustrating embodiments of the present invention.
Figure 6:
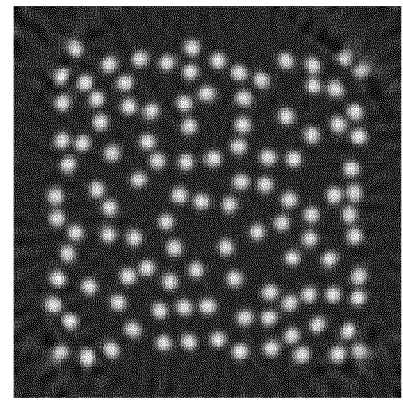
Figure 7:
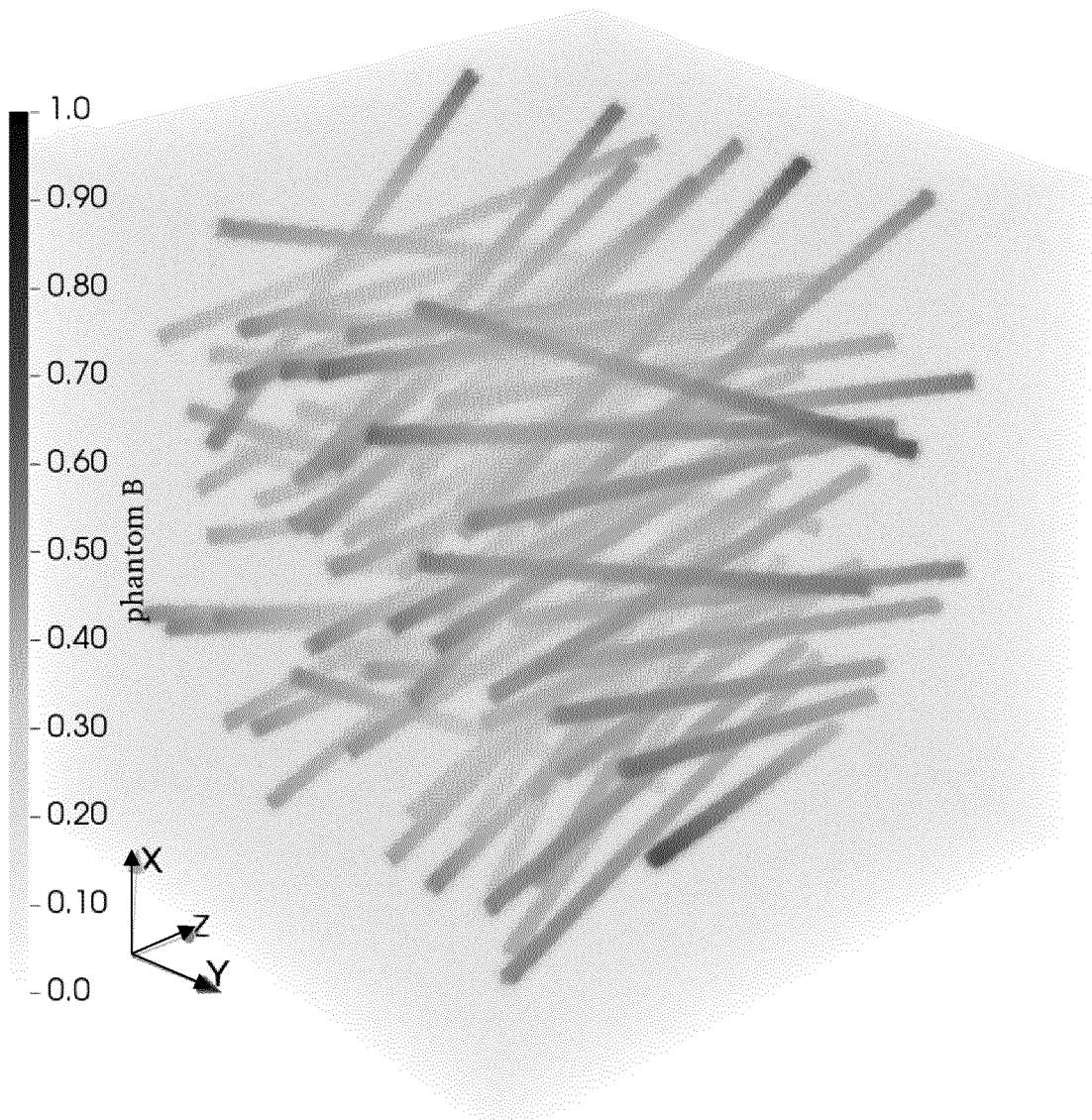
FIG. 7 illustrates a rendering of the ground truth of the second synthetic phantom, in an example illustrating embodiments of the present invention.

From those phantoms, forward projection images were created using a simulated cone-beam geometry, which is the most commonly used geometry in industrial and desktop X-ray scanners. The phantom was placed in the origin of the system. The source-detector distance (SDD) was 250 mm and the source object distance (SOD) was 14 mm. The simulated detector had square pixels with a size of 50 µm. This yielded an effective detector pixel size of 2.8 µm isotropic in the reconstructions, with a magnification of around 17.86 in the center plane of the phantom. In FIG. 5 and FIG. 6, the central slice along the yz-plane of the randomly generated phantom 'phantomA' and the same slice of a reconstruction of said phantom from simulated projections are respectively shown. FIG. 7 illustrates a rendering of the ground truth of the synthetic 'phantom B' with 72 individual fibers with directions drawn from $f(u,\mu=(0,0), \kappa=7)$.

Using the generated data, the performance of the PARE method is evaluated as a function of both the number of projection angles available and the signal-to-noise (SNR). In all cases, 100 SIRT iterations were chosen as the base line for the reconstructions of the two generated phantoms. We performed one experiment for each noise level a and number of projections, respectively for both phantoms. For the experiments with added noise, additive Gaussian distributed white noise was used, which was added to the projection data before the reconstruction.

The errors in the parameter estimates obtained by PARE are discussed hereinbelow. The errors in the length and centroid position coordinates of the fibers were obtained by computing the difference between the estimates of these parameters and their corresponding ground-truth values. The errors in the direction vectors were computed as the angle derived from the dot product of the Cartesian representation of the estimated and ground truth vector, respectively. It should be noted that prior to the computation of these errors, it was first needed to identify which estimated fiber parameter vector corresponded with which ground truth fiber parameter vector.

To this end, each ground truth fiber parameter vector was matched with the vector in the set of estimated fiber parameter vectors that is closest in terms of Euclidean distance. Mathematically, the one-to-one mapping performed can be described as follows. Let the sets of fibers be denoted as F_gt and F_est, the ground truth and estimated fibers respectively, then the mapping from one set to the other is defined as $$f : \forall a_n \in F_{gt} \mapsto \arg\min_{b \in F_{est}\setminus\{f(a_1, \ldots, a_{n-1})\}} \|a_n - b\|^2. \quad (14)$$

It is to be noted that this implies that the mapping depends on the order of processing if two or more fibers from one set have the same distance to one single fiber in the other set. This case can be expected to be highly unlikely and even if it occurs, the error value will presumably be the same for all of them, so the order is not important.

If there were less or more fibers detected than are in the ground truth, only the ones that fit best were mapped and the others were discarded as undetected. In the former case we only evaluate the error on the fibers that have an estimate associated with them, and in the latter case, associated fibers were found for each ground truth fiber and the rest was not evaluated.

Figure 8:
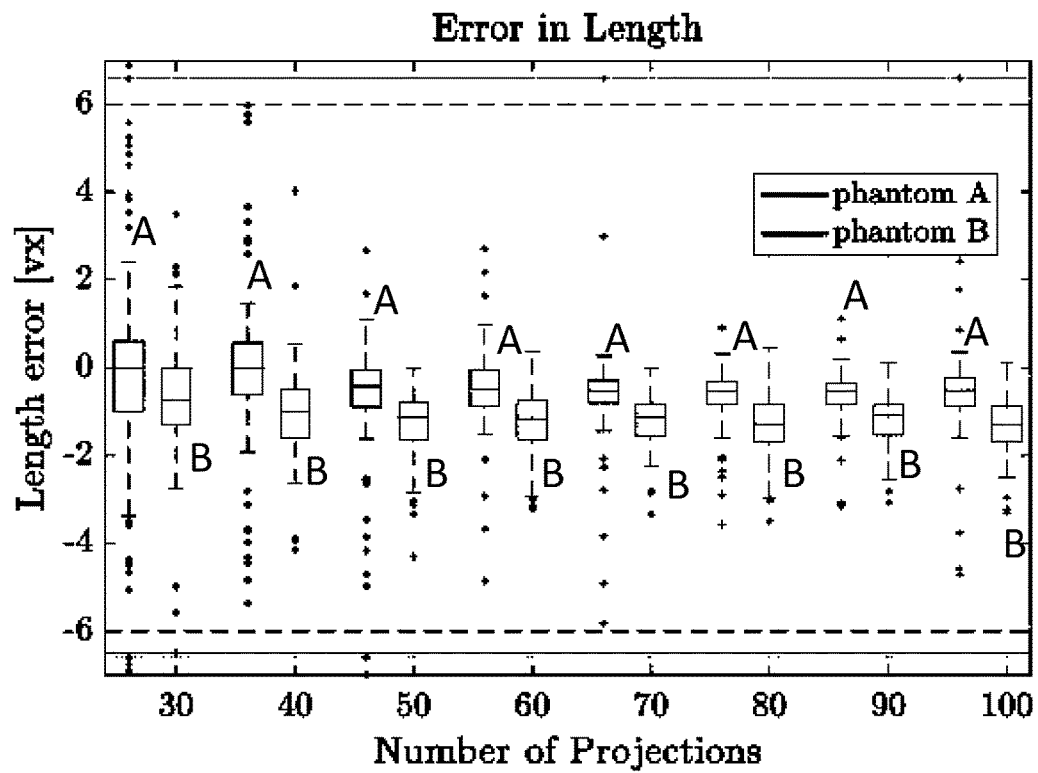
FIG. 8, FIG. 9 and FIG. 10 show respectively a length error, a direction error and centroid position errors of an estimation of fiber parameters, in an example illustrating embodiments of the present invention.
Figure 9:
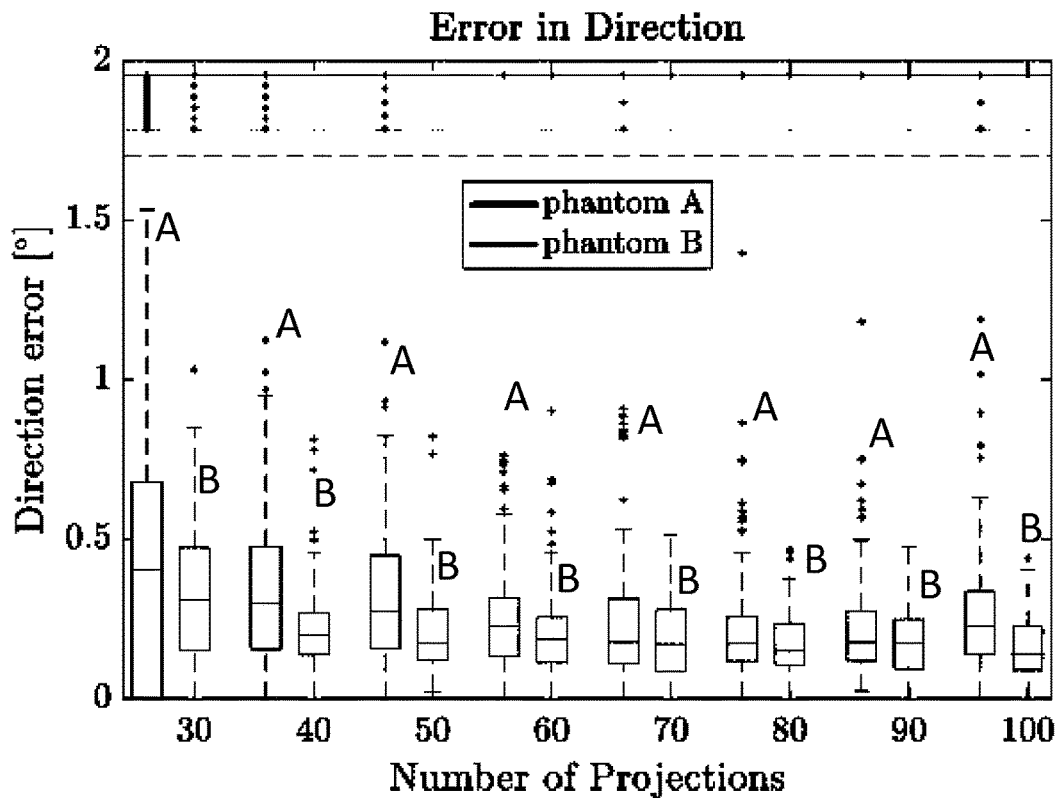
Figure 10:
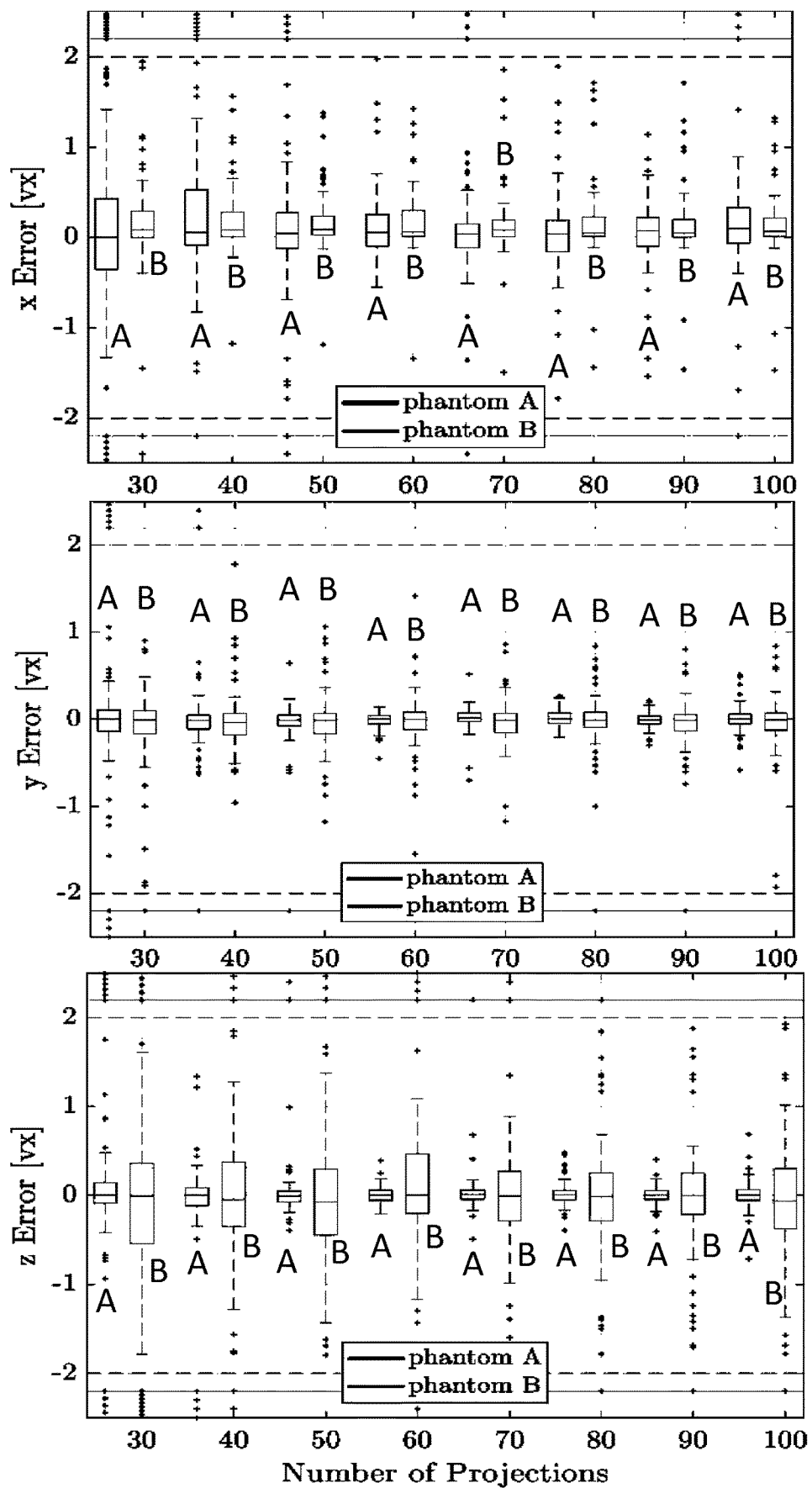

In FIG. 8, FIG. 9 and FIG. 10, the quality of the estimation with PARE as function of the number of used projections is shown. FIG. 8 shows the length error for varying number of projections on 'phantoms A and B' with respect to the estimated fiber length. Outliers were capped at +/−6 vx, but are still shown outside the horizontal dotted lines. FIG. 9 shows the direction error for varying number of projections on 'phantoms A and B' with respect to the estimated direction vector. Outliers were capped at 2°, but are still shown outside the horizontal dotted lines. FIG. 10 shows centroid position errors for varying number of projections on both 'phantoms A and B' with respect to the estimated centroid position of the fiber. Outliers were capped at +/−2 vx, but are still shown outside the horizontal dotted lines.

In all figures there are two box plots for each projection, where the darker one corresponds to results for 'phantom A' and the lighter one corresponds to 'phantom B'. It can clearly be seen that the algorithm can retrieve the individual fiber centroids with around +/−0.5 vx accuracy in the upper and lower quartiles even with as low as 30 projections for both phantoms.

As can be observed from FIG. 10, errors are higher in the coordinate direction that corresponds to the mean axis of the direction distribution. While the direction estimation is not affected by this, the length estimation and centroid estimation are correlated. The length estimation can retrieve the fiber length up to +/−1 vx for 30 projections. The direction vector can be approximated to about 0.6° for the upper quartile.

With an increasing number of projections this error naturally decreases, as there is more information available for computing the projection error making the procedure more sensitive to small parameter changes. With 100 projections, the error for the centroid position is as low as +/−0.3 vx which is around the accuracy of the sub-sampling performed for the voxelization of the fibers in the phantoms. The direction can be estimated to around 0.4° for 'phantom A' and 0.25° for 'phantom B'. Lengths are estimated between 0.2 vx and 0.7 vx for 'phantom A' and between 0.9 vx and 1.8 vx for 'phantom B'.

Figure 11:
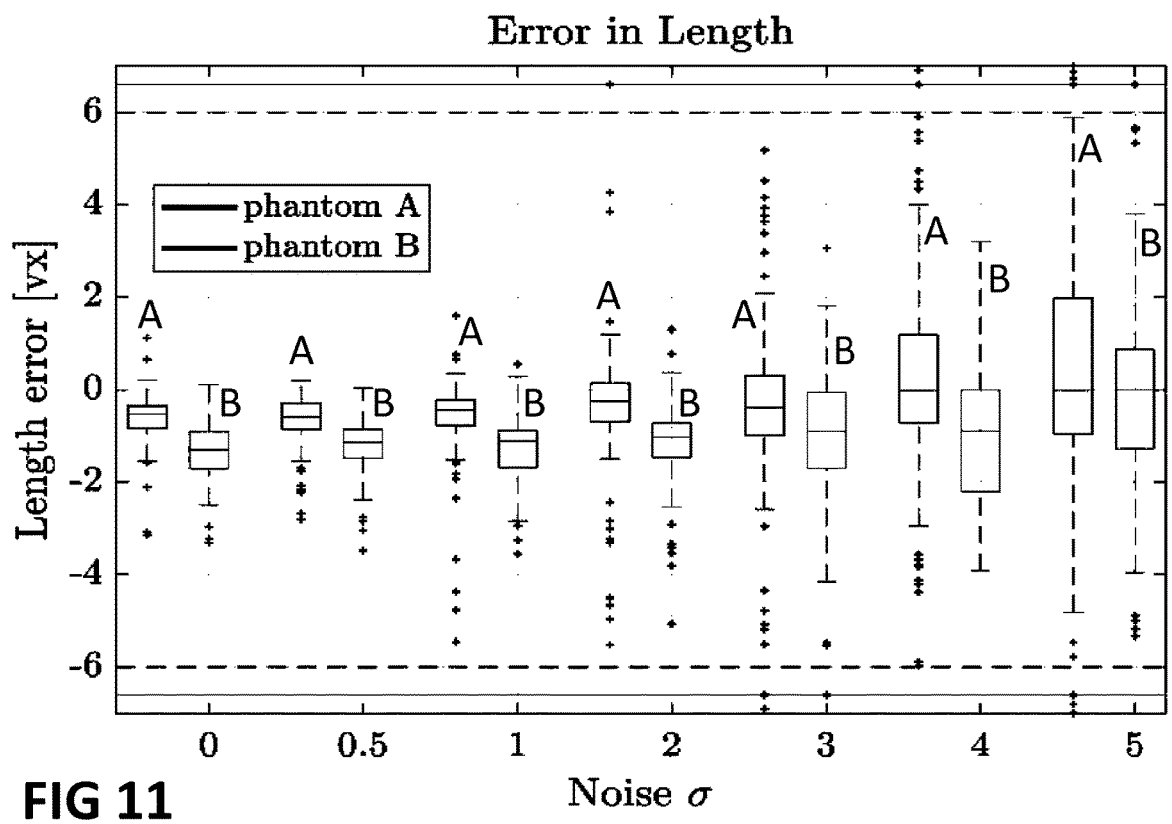
FIG. 11, FIG. 12 and FIG. 13 show respectively the length, direction and position errors as function of a standard deviation of additive noise added to the projection data, in an example illustrating embodiments of the present invention.
Figure 12:
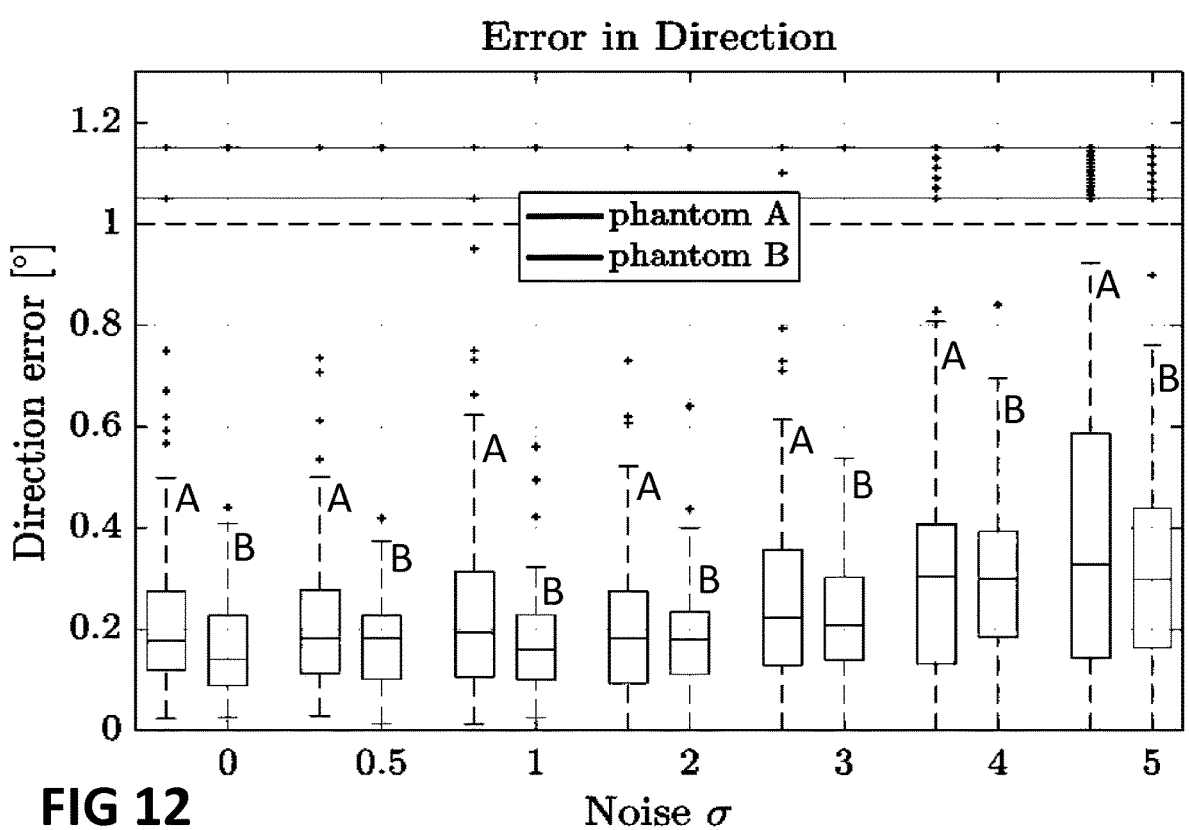
Figure 13:
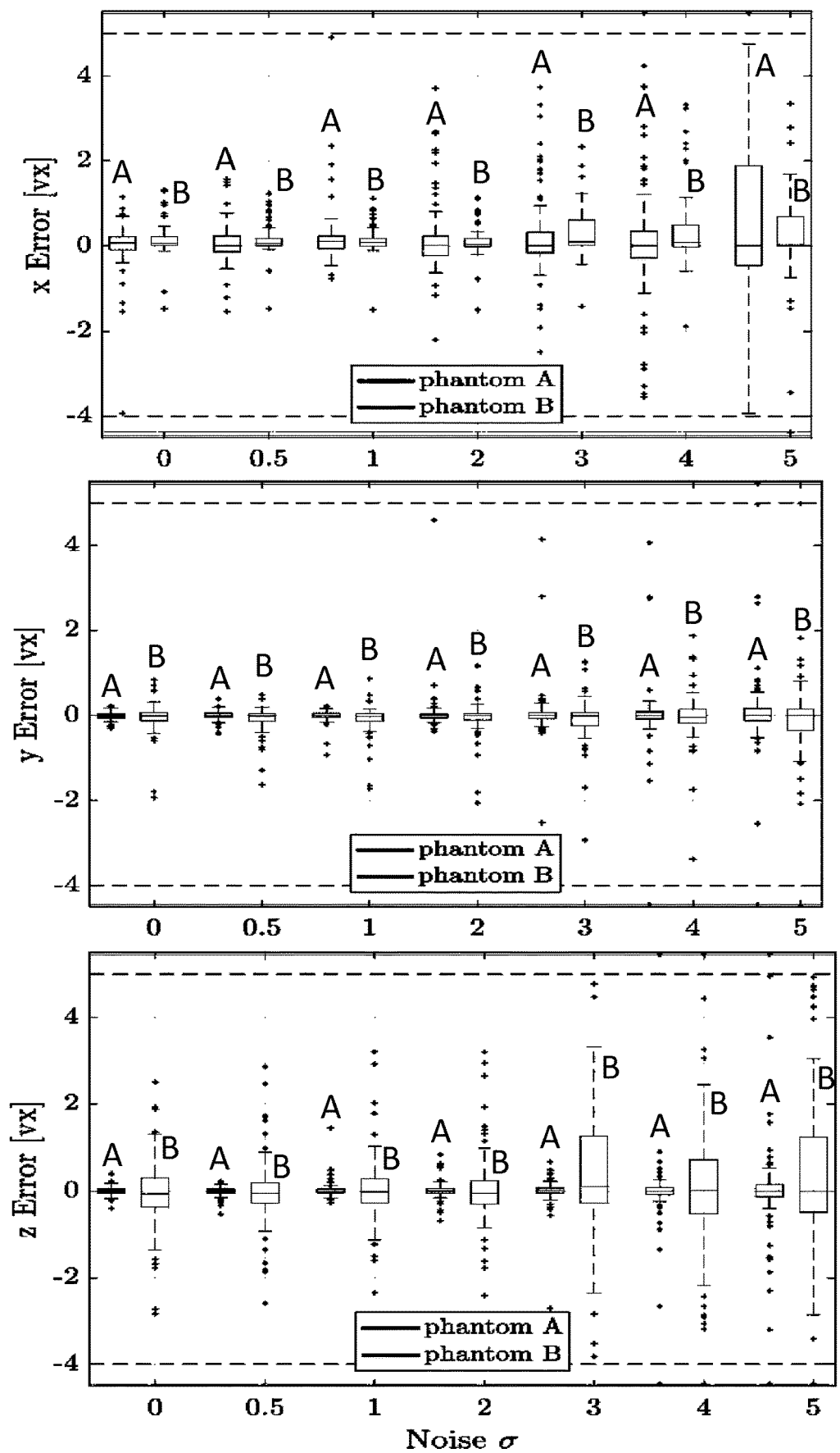

In FIG. 11, FIG. 12 and FIG. 13, respectively the length, direction and position errors are shown as function of the standard deviation a of the additive noise that was added to the projection data.

The length error for several noise levels on 'phantoms A and B' with respect to the estimated fiber length is shown in FIG. 11. Outliers were capped at +/−6 vx, but are still shown outside the horizontal dotted lines. The direction error for several noise levels on 'phantoms A and B' with respect to the estimated direction vector is shown in FIG. 12. Outliers were capped at 1°, but are still shown outside the horizontal dotted lines. The centroid position error for several noise levels on both 'phantoms A and B' on the estimated centroid position of the fiber is shown in FIG. 13. Outliers were capped at +/−4 vx, but are still shown outside the horizontal dotted lines.

As expected, the errors increase for increasing σ. The length estimates are barely changing for the lower noise levels σ=0.5 and σ=1.0 and are in the same range as the errors for 100 projections in the previous tests. This is also expected, since 100 projections were used consistently for this experiment. The signal-to-noise ratio (SNR) for the different noise levels and phantoms are laid out in the table hereinbelow. This was computed by $$SNR = 10\log\left(\frac{\mu_{signal}}{\sigma_{noise}}\right), \quad (15)$$

where $\mu\_signal$ is the mean of the measured intensity of the projections and $\sigma\_noise$ the corresponding noise level. The length and the centroid estimates seem to be more affected by the noisy projections than the direction estimates.

| σ | $SNR_A$ | $SNR_B$ |
|---|---|---|
| 0.5 | 17.06 dB | 16.88 dB |
| 1.0 | 14.05 dB | 13.87 dB |
| 2.0 | 11.04 dB | 10.86 dB |
| 3.0 | 9.27 dB | 9.10 dB |
| 4.0 | 8.03 dB | 7.85 dB |
| 5.0 | 7.06 dB | 6.88 dB |

In the case of the highest noise level, the length estimate is 2 vx overestimated in the upper quartile for 'phantom A' and around 1 vx for 'phantom B'.

This is likely due to the way voxels change in the simulated projections of our model. When varying the direction vector, more voxels change their value, compared to when the length or centroid position is changed. This in turn means that the optimization is more sensitive to small changes in direction, especially when the fibers are very long.

Figure 14:
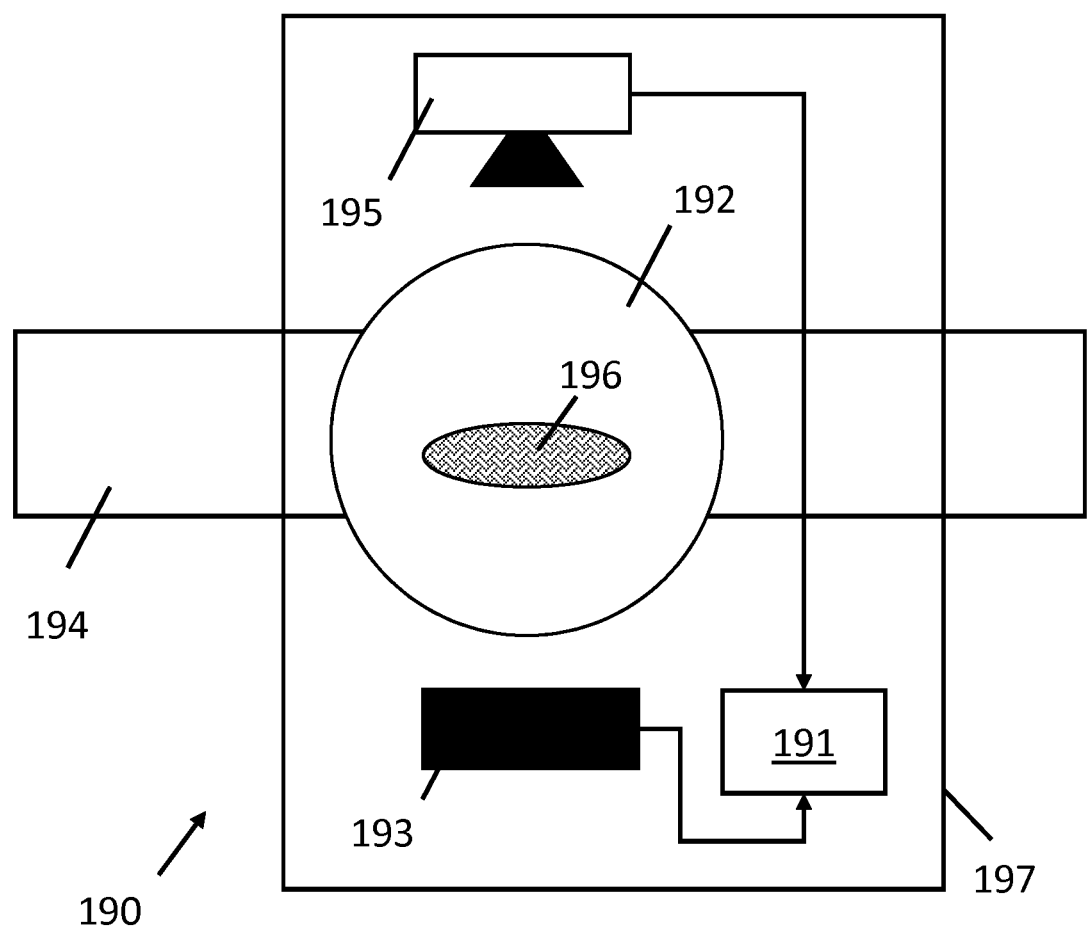
FIG. 14 illustrates an inspection system as can be used in embodiments of the present invention.

Referring now to FIG. 14, an inspection system 190 is shown which comprises a radiation imaging device and a processor 191. The radiation imaging device may be a stationary X-ray imaging device comprising an X-ray source 195 and a detector 193 sensitive to X-rays. The detector 193 and the source 195 are operatively connected to the processor 191 for transmitting acquired projection images of an item 196 under inspection, e.g. a fiber-reinforced workpiece, and for communication operating parameters. The item 196 under inspection may be temporarily secured on a turntable, e.g. in a holder or securing frame, to obtain projection images for different projection angles. The radiation imaging device 190 is shielded by a shielding enclosure 197 which protects human operators and other equipment from scattered X-ray radiation. The processor 191 is adapted for performing the remaining method steps described before. The item 196 may be brought to the radiation imaging device 190 by way of a conveyor belt 194 or an equivalent item transfer means, e.g. a robotic arm. This example is particularly suited for inline inspection of items in an industrial process. In an alternative inspection system, the radiation imaging device may comprise a rotating gantry or a micro-CT scanner if the inspected items are of sufficiently small size to be loaded into the micro-CT scanner.

Although the foregoing example extensively described X-ray radiation imaging, other radiation imaging modalities may be employed, including for example terahertz imaging for items that are weakly absorbing in the terahertz wavelength band, e.g. items that are at least partially translucent with respect to terahertz radiation. Textiles, fabrics, and other items comprising fiber-containing materials are often translucent in respect of terahertz radiation. Likewise, methods and systems may be used for gamma radiation, or even visible radiation in cases in which the inspected item is translucent or partially translucent at visible wavelengths and only weakly scattering, e.g. in the geometric optics limit the scattering contribution is often neglectable.

The invention claimed is:

1. A method for inspection of an item, the method comprising:
    acquiring a plurality of projection images of said item at a plurality of projection angles, using a radiation imaging device;
    obtaining a tomographic reconstruction based on said plurality of projection images;
    detecting a plurality of objects in said tomographic reconstruction, each of said plurality of objects having a generic shape described by a parametric three-dimensional numerical model, wherein said detecting comprises determining initial estimates of position and/or orientation of each of said plurality of objects and at least one geometrical parameter of said three-dimensional model for each of said plurality of objects;
    iteratively refining said initial estimates by using a projection-matching approach, wherein said refining comprises, at each iteration, simulating forward projection images according to operating parameters of the radiation imaging device at said plurality of projection angles for at least one of the plurality of objects, and reducing a difference metric between acquired projection images and simulated forward projection images.

2. The method of claim 1, wherein said determining of said initial estimates comprises determining a center position and a direction of each of said plurality of objects and a length and/or a radius of each of said plurality of objects.

3. The method of claim 1, wherein said objects represent fibers.

4. The method of claim 1, wherein acquiring said plurality of projection images comprises performing a computed tomography scan of the item.

5. The method of claim 1, wherein said plurality of projection images consists of a number of projection images, wherein said number lies in the range of 5 to 1000.

6. The method of claim 1, wherein said detecting comprises segmenting said objects from an image background in said tomographic reconstruction using a template matching approach for matching of the tomographic reconstruction to one or more templates for the numerical model of each object shape, or by applying the tomographic reconstruction as input to a machine learning algorithm trained on models of object shapes.

7. The method of claim 6, wherein said detecting comprises determining said initial estimate of said position of each of said objects, and subsequently detecting said orientation of each of said objects taking the determined initial estimate of said position into account.

8. The method of claim 7, wherein said detecting of said orientation comprises performing an iterative Hough Transform algorithm for three-dimensional line segments.

9. The method of claim 7, wherein said detecting comprises determining an initial estimate of a length of each of said objects after determining said initial estimate of said orientation.

10. The method of claim 9, wherein said determining said initial estimate of said length comprises an edge detection on a line profile in a resultant image of the template matching at said initial estimate of said position in the direction corresponding to said initial estimate of said orientation.

11. The method of claim 10, comprising applying a median filter to said line profile and/or smoothing said line profile using a Gaussian filter.

12. The method of claim 10, comprising determining inflection points on either end of said line profile, wherein determining said inflection points comprises determining candidate inflection points and rejecting candidate inflection points for which a slope is below a predetermined threshold.

13. The method of claim 12, wherein said predetermined threshold is a predetermined value between an expected attenuation value of a background material in said item and an expected attenuation value of said detected objects.

14. The method of claim 1, wherein said iteratively refining of said initial estimates comprises a numerical optimization of parameters comprising said position and/or orientation of each of said plurality of objects and said least one geometrical parameter for each of said plurality of objects using said initial estimate as initialization parameters for said numerical optimization.

15. A system comprising a radiation imaging device and a processor, wherein said radiation imaging device is adapted for acquiring said plurality of projection images of said item at a plurality of projection angles in a method in accordance with claim 1, and wherein said processor is adapted for performing the remaining steps of said method taking operating parameters of the radiation imaging device into account.

16. A data storage device comprising a computer program product for implementing, when executed on a processor, a method in accordance with claim 1 when provided with a plurality of acquired projection images and operating parameters of a radiation imaging device as input.

* * * * *